(12) United States Patent
Dininno et al.

(10) Patent No.: US 6,288,054 B1
(45) Date of Patent: *Sep. 11, 2001

(54) CARBAPENEM ANTIBACTERIAL COMPOUNDS, COMPOSITIONS CONTAINING SUCH COMPOUNDS AND METHODS OF TREATMENT

(75) Inventors: Frank P. Dininno, Old Bridge; Milton L. Hammond, Somerville; Kevin D. Dykstra, West Milford, all of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,777

(22) Filed: May 24, 1999

Related U.S. Application Data

(60) Provisional application No. 60/087,726, filed on Jun. 2, 1998.

(51) Int. Cl.[7] ............ C07D 477/14; C07D 519/06; A61K 31/428; A61P 31/04; C07F 7/18
(52) U.S. Cl. ...................... 514/210.09; 540/302
(58) Field of Search ................ 540/302; 514/210, 514/210.09

(56) References Cited

U.S. PATENT DOCUMENTS

| 3,654,296 | 4/1972 | Christensen | 260/304 |
|---|---|---|---|
| 4,309,438 | 1/1982 | Christensen et al. | 424/274 |
| 4,479,947 | 10/1984 | Christensen | 424/203 |

FOREIGN PATENT DOCUMENTS

| 0 007 614 | 2/1980 | (EP) . |
|---|---|---|
| 0 072 014 | 2/1983 | (EP) . |
| 8-41063 | * 2/1996 | (JP) . |

OTHER PUBLICATIONS

S. M. Schmitt et al., *J. Antibiotics* 41(6): 780–787 (1988).
Michael E. Jung & Lyn A. Light, *Tet. Ltrs.*, 23(38): 3851–3854 (1982).
Keving D. Dykstra & Frank Dininno, *Tet. Ltrs.* 39: 1865–1868 (1998).

* cited by examiner

*Primary Examiner*—Mark L. Berch
(74) *Attorney, Agent, or Firm*—Sylvia A. Ayler; Mark R. Daniel

(57) ABSTRACT

The present invention relates to tricyclic carbapenem antibacterial agents in which the carbapenem nucleus is fused to a 6 membered carbocyclic ring. The compound is further substituted with various substituent groups including at least one cationic group.

The compounds are represented by formula I:

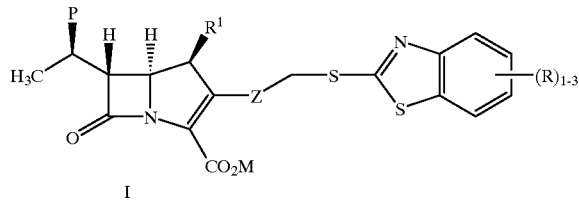

Pharmaceutical compositions and methods of use are also included.

25 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional Application No. 60/087,726, filed Jun. 2, 1998.

BACKGROUND OF THE INVENTION

The present invention relates to carbapenem antibacterial agents in which the carbapenem nucleus is substituted at the 2-position with a 2-mercaptobenzothiazole moiety linked through a group —Z—$CH_2$—. Z represents an trans-ethenediyl group, ethynediyl group or is absent. The mercaptobenzothiazole moiety is further substituted with various substituent groups including at least one cationic group.

The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The present invention relates to anti-MRSA carbapenem antibiotics containing heteroaromatic based side-chains. The side-chain imparts MRS activity previously unassociated with the carbapenem skeleton.

The compounds of the invention are represented by formula I:

[Structure I: carbapenem with $H_3C$, P, H, H, $R^1$, Z, S, benzothiazole with $(R)_{1-3}$, $CO_2M$]

I or a pharmaceutically acceptable salt thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

Z represents trans-ethenediyl, ethynediyl or is absent;

each R is independently selected from: —R*; —Q; hydrogen; halo; —CN; —$NO_2$; —$NR^aR^b$; —$OR^c$; —$SR^c$; —C(O)$NR^aR^b$; —C(O)$OR^h$; —S(O)$R^c$; $SO_2R^c$; $SO_2NR^aR^b$; $NR^aSO_2R^b$; —C(O)$R^a$; —OC(O)$R^a$; —OC(O)$NR^aR^b$; —$NR^aC(O)NR^bR^c$; —$NR^aCO_2R^h$; —$OC_2R^h$; —$NR^aC(O)Rb^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —N+$(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

[Five heterocyclic cation structures with labels α, β, δ, σ, λ, μ, and $(CH_2)_b$, $(CH_2)_a$, $R^x$, $NR^xR^yR^z$, $L^{\ominus}$]

wherein:

a and b are 1, 2 or 3;

$L^-$ is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

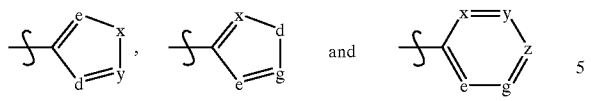

wherein:
d represents O, S or $NR^k$;
e, g, x, y and z represent $CR^m$, N or $N^+R^k$, provided that no more than one of e, g, x, y and z in any given structure represents $N^+R^k$;
$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;
each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;
$R^n$ and $R^o$ represent hydrogen, phenyl; —$C_{1-6}$ straight- or branched-chain alkyl unsubstituted or substituted with one to four $R^i$ groups;
each $R^s$ independently represents hydrogen; phenyl or —$C_{1-6}$ straight- or branched-chain alkyl, unsubstituted or substituted with one to four $R^i$ groups;
each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;
$R^u$ and $R^v$ represent hydrogen or —$C_{1-6}$ straight- or branched-chain alkyl, unsubstituted or substituted with one to four $R^i$ groups;
or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;
each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;
or $R^h$ and $R^w$ taken together with any intervening atoms represent a 5–6 membered saturated ring, optionally interrupted by one or two of O, S, $SO_2$, NH or $NCH_3$;
$R^x$ represents hydrogen or a $C_{1-8}$ straight- or branched-chain alkyl, optionally interrupted by one or two of O, S, SO, $S_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;
$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;
or $R^x$ and $R^y$ together with any intervening atoms represent a 4–6 membered saturated ring optionally interrupted by O, S, $S_2$, $NR^w$, $N^+R^hR^w$ or —C(O)—, unsubstituted or substituted with 1–4 $R^i$ groups,
and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

Pharmaceutical compositions and methods of treatment are also included herein.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical, straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

 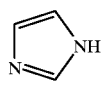 

pyrrole (pyrrolyl)    imidazole (imidazolyl)    thiazole (thiazolyl)

  

oxazole (oxazolyl)    furan (furyl)    thiophene (thienyl)

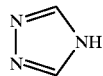 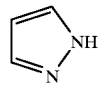 

triazole (triazolyl)    pyrazole (pyrazolyl)    isoxazole (isoxazolyl)

  

isothiazole (isothiazolyl)    pyridine (pyridinyl)    pyrazine (pyrazinyl)

 

pyridazine (pyridazinyl)    pyrimidine (pyrimidinyl)

triazine (triazinyl)

Heteroarylium refers to heteroaryl groups bearing a quaternary nitrogen atom and thus a positive charge. Examples include the following:

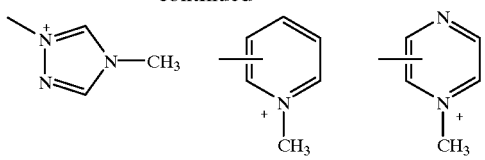

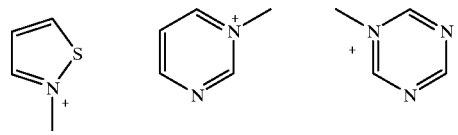

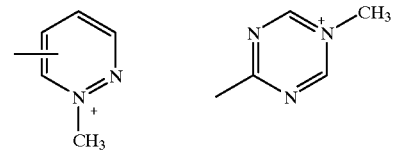

When a charge is shown on a particular nitrogen atom in a ring which contains one or more additional nitrogen atoms, it is understood that the charge may reside on a different nitrogen atom in the ring by virtue of charge resonance that occurs.

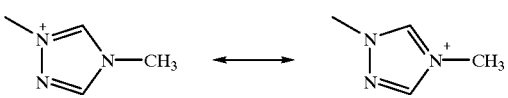

and

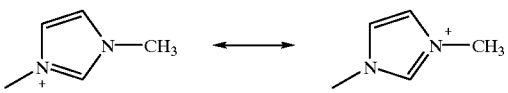

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

When an alkyl group is "interrupted by" 1 or more moieties, such as O, S, N, —C(O)— and the like, this includes alkyl groups which are terminated by the moiety or moieties, as well as alkyl groups that are interrupted or terminated by combinations of such groups. Thus for example, —C(O)O—, —OC(O)—, —C(O)NR$^8$— and similar such moieties are included. Examples of alkyl groups terminated by the moiety or moieties are as follows: —O—C$_{1-6}$ alkyl, —C$_{1-6}$ alkyl-O—, —C$_{1-6}$ alkyl-OC(O)—, —O—C$_{1-6}$ alkyl-S— and the like. Obviously other moieties are included in accordance with the general description contained herein.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBS), phenacyl, p-methoxybenzyl, o-nitrobenzyl, p-methoxyphenyl, p-nitrobenzyl, 4-pyridylmethyl and t-butyl.

Examples of suitable hydroxyl protecting groups include triethylsilyl (TES), t-butyldimethylsilyl (TBS), t-butyldiphenylsilyl (DPTBS), o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —CO$_2$M, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309, 438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

L$^-$ can be present or absent as necessary to maintain the appropriate charge balance. When present, L$^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L− represents a specie with more than one negative charge, such as malonate, tartrate or ethylenediamine-tetraacetate (EDTA), an appropriate number of carbapenem molecules can be found in association therewith to maintain the overall charge balance and neutrality.

At least one of the R groups attached to the phenoxy platform can optionally contain a positively charged moiety. Thus, it can include —R* or Q, or a moiety which in turn contains a positively charged group.

A subset of compounds of formula I which is of interest relates to those compounds where $CO_2M$ represents a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of formula I which is of interest relates to compounds wherein one R represents a group which contains a positively charged moiety, and the remaining R groups are selected from hydrogen and $C_{1-6}$ straight or branched chain alkyl, unsubstituted or substituted with one to four $R^d$ groups. More particularly, this subset of interest includes compounds of formula Ia wherein one R represents a group containing a positively charged moiety and the remaining R groups are hydrogen.

With respect to the positively charged moiety or moieties that are contained in one or more R groups, it is preferred that from 1–3 positive charges be present, and most preferably 1–2 positive charges be present, balanced by the carboxylate anion and a negatively charged counterion.

Another subset of compounds which is of interest is represented by formula I wherein one R group represents a —$C_{1-6}$ straight or branched chain alkyl group, substituted with one to four $R^d$ groups, wherein one $R^d$ group represents —R* or Q. Hence, a positively charged moiety —R* or Q is attached to an alkyl group.

Another group of compounds of interest is represented by formula I wherein Q is selected from the group consisting of:

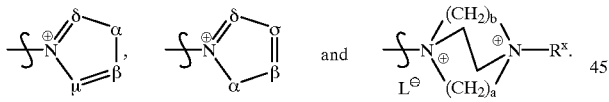

More particularly, the group of compounds which is of interest is represented by formula I wherein Q represents:

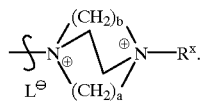

Within this subset of compounds, L−, a and b are as originally defined, and $R^x$ is as originally defined, and represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups.

Another group of compounds of interest is represented by formula I wherein Q represents —$N^+R^xR^yR^z$, wherein $R^x$, $R^y$ and $R^z$ are as originally defined.

Another group of compounds of interest is represented by formula I wherein one R* group is present and is selected from:

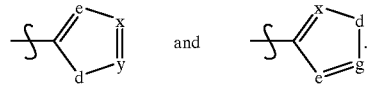

Within this subset, d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Another group of compounds of interest is represented by formula I wherein R is A—$(CH_2)_n$—Q, wherein A is O, S, or $CH_2$, n is 0–3 and Q is as originally defined.

Another group of compounds of interest is represented by formula I wherein Z is trans-CH=CH and all other variables are as originally described.

Another group of compounds of interest is represented by formula I wherein Z is —C≡C— and all other variables are as originally described.

Another group of compounds of interest is represented by formula I wherein Z is absent and all other variables are as originally described.

A preferred subset of compounds of formula I which is of particular interest relates to compounds represented by formula Ia Ia

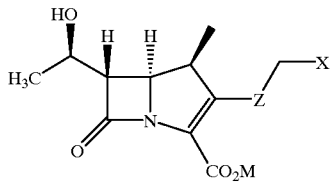

wherein X is:

1

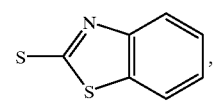

2

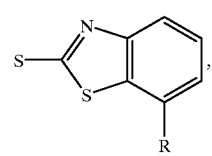

3

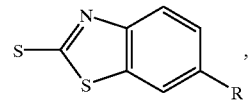

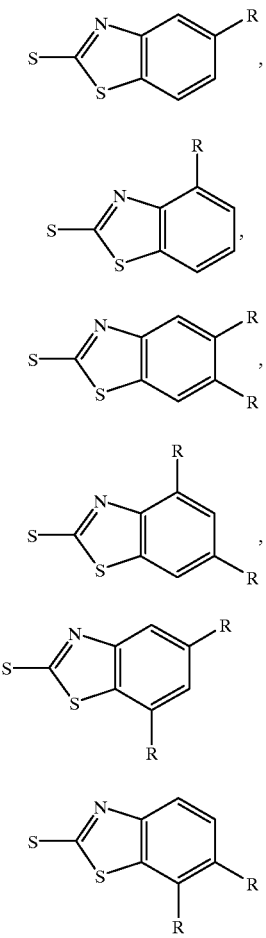

wherein:
  Z is as originally described;
  $CO_2M$ represents a carboxylate anion;
  R group may contain a positively charged moiety;
  $R^d$ is as originally defined;
  $R^h$ represents hydrogen or a $C_{1-6}$ straight or branched chain alkyl group;
  Q is selected from the group consisting of:

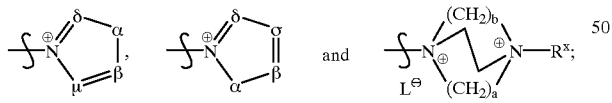

wherein L–, a and b are as originally defined, and $R^x$ represents a member selected from the group consisting of: hydrogen or a $C_{1-8}$ straight- or branched-chain alkyl, optionally interrupted or terminated by one or two of O, S, SO, $S_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;
  R* is selected from:

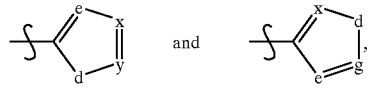

wherein d represents $NR^{k-}$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Another preferred subset of compounds of formula Ia is realized when X is 4, 6 or 8 wherein R contains a positively charged moiety selected from the group consisting of: —R*, Q, A—$(CH_2)_n$—Q, and a $C_{1-6}$ straight or branched alkyl chain substituted with one $R^d$ group, wherein A is as originally described $R^d$ is independently selected —R* or Q;
  Q is selected from the group consisting of:

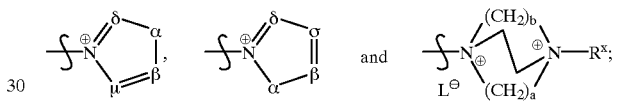

wherein L–, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;
  R* is selected from:

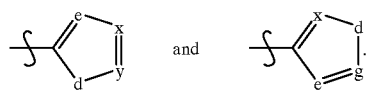

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

An even more preferred subset of formula Ia is realized when X is 4.

Another preferred subset of compounds of formula Ia is realized when X is 3, 7, or 9 and at least one R contains a positively charged moiety selected from the group consisting of: —R*, Q, A—$(CH_2)_n$—Q, and a $C_{1-6}$ straight or branched alkyl chain substituted with one $R^d$ group, wherein A is as originally described $R^d$ is independently selected —R* or Q;

Q is selected from the group consisting of:

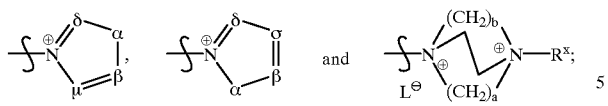
and wherein L–, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Another more preferred subset of compounds of the invention is represented by formula Ib:

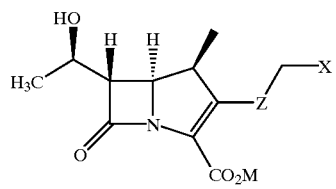

Ib wherein X is:

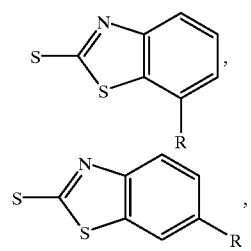

2

3

-continued

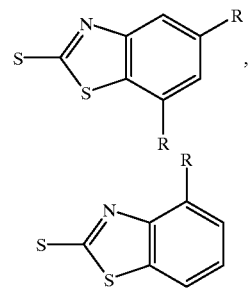

4

5 wherein:

R represents

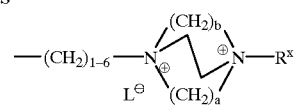

and $R^x$, a, b and L– are as originally defined.

Another more preferred subset of the compounds of formula Ib is realized when:

R represents A—$(CH_2)_n$—Q, wherein A is O, S, or $CH_2$, n is 0–3 and Q is selected from the group consisting of:

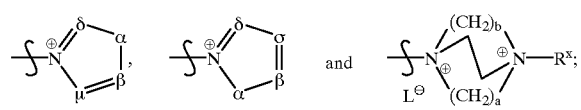

wherein L–, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups.

Within the subsets, all other variables are as originally defined with respect to formula I.

R presentative examples of compounds of the invention are shown below. The invention is intended, where appropriate, to include protonated amines protonated at the appropriate pH, e.g., pH 7.

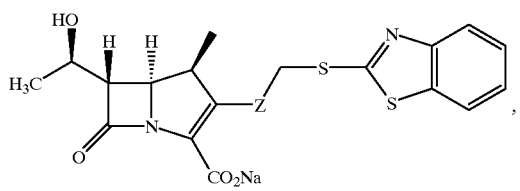

E-1

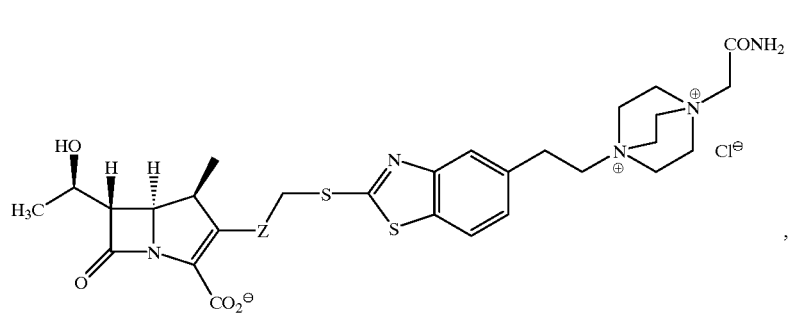
E-2
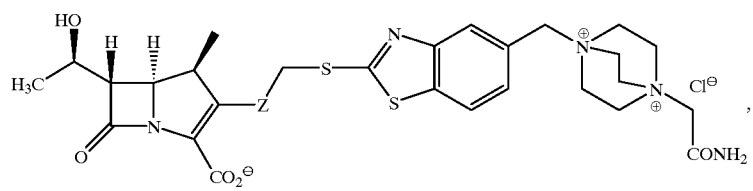
E-3
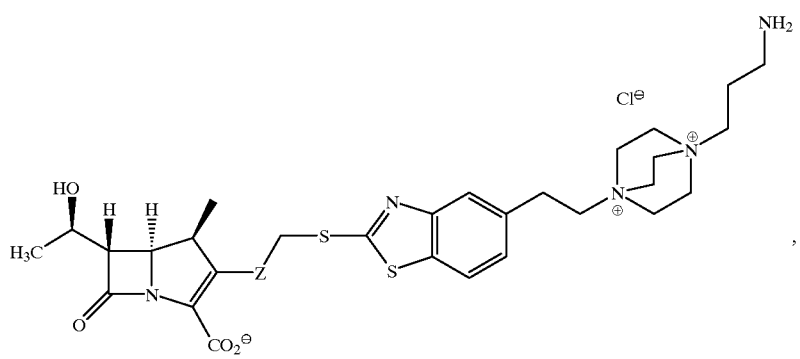
E-4
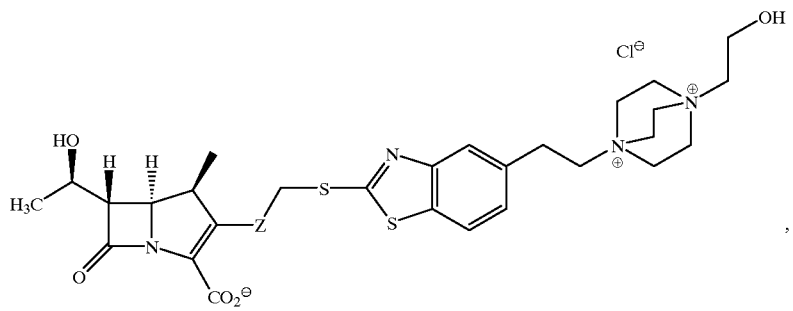
E-5
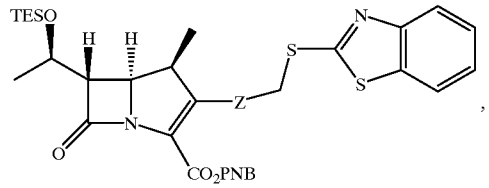
E-6
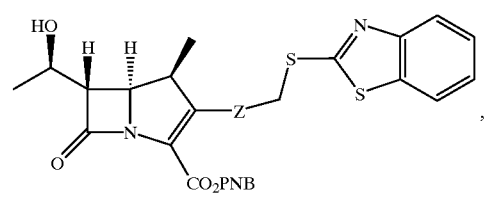
E-7

-continued
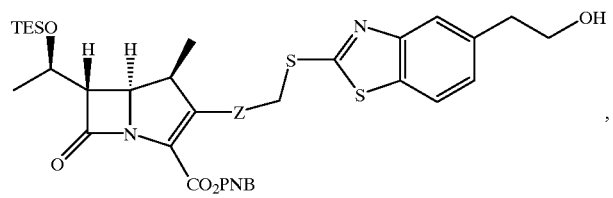
E-8
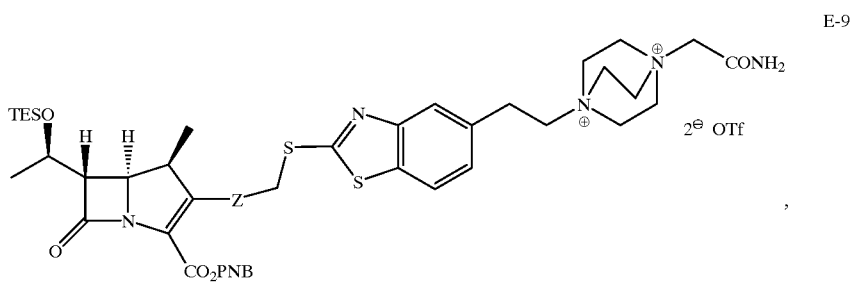
E-9
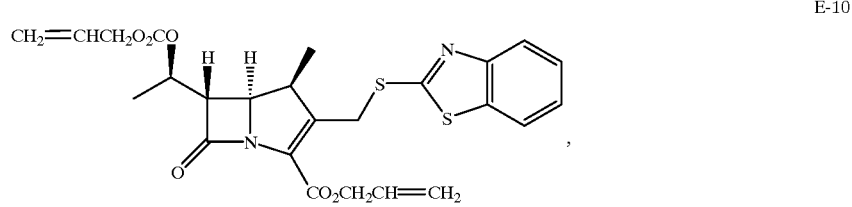
E-10
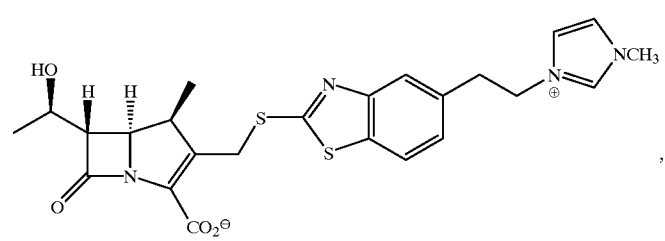
E-11
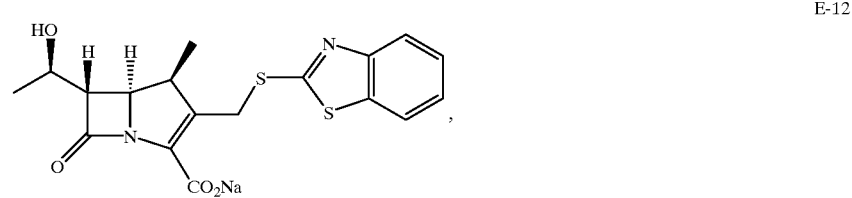
E-12
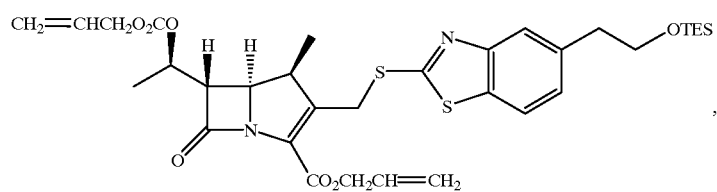
E-13
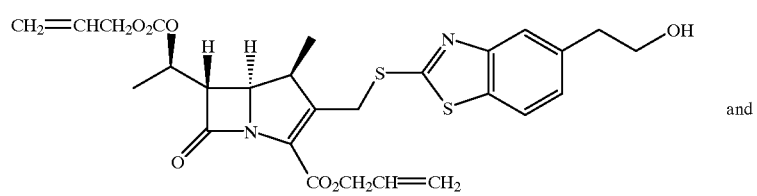
E-14
and

E-15

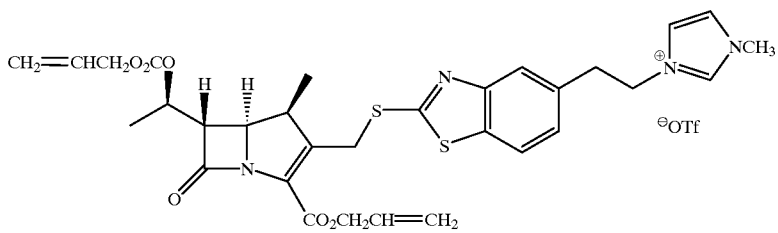

or a pharmaceutically acceptable salt thereof, wherein Z represents trans-ethenediyl, ethynediyl or absent.

The compounds of the present invention are prepared by two basic processes which are illustrated by the following generic schemes:

The compounds of the present invention are prepared as depicted in Flow sheets A, B, C and D. The vinyl linked carbapenems are prepared, as shown in Flow sheet A, by reacting a suitably protected, activated 2-triflyl-carbapen-2-em-3-carboxylate A1 with a hydroxy allylic trialkyl stannane, to produce A2, and then reacting the condensed biaryl under Mitsunobu conditions to produce A3. Removing any protecting groups which are present affords the desired final vinylic product A4.

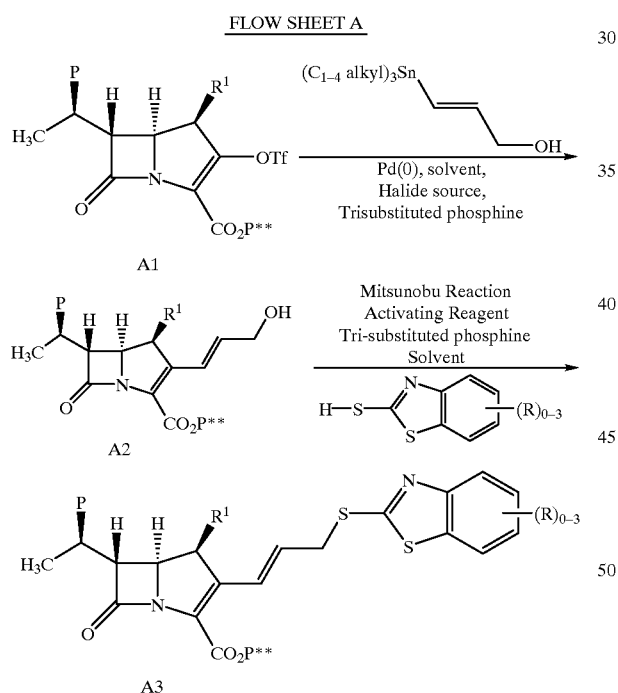

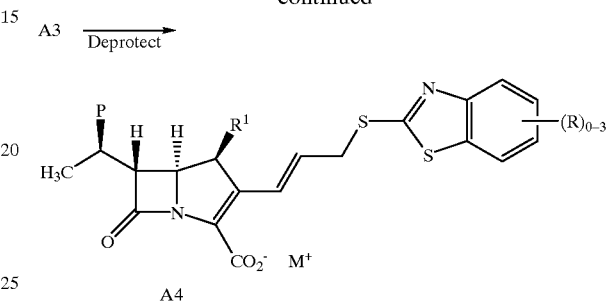

The acetylenic linked carbapenems are prepared as shown in Flow sheet B in which intermediate A1 is reacted with a protected hydroxy propargylic trialkyl stannane to produce A5, deprotecting the propargylic hydroxy group to produce A6, and then reacting the 2-mercaptobenzothiazole moiety under Mitsunobu conditions to produce A7. Removing any protecting groups which are present affords the desired final acetylenic product A8.

FLOW SHEET B

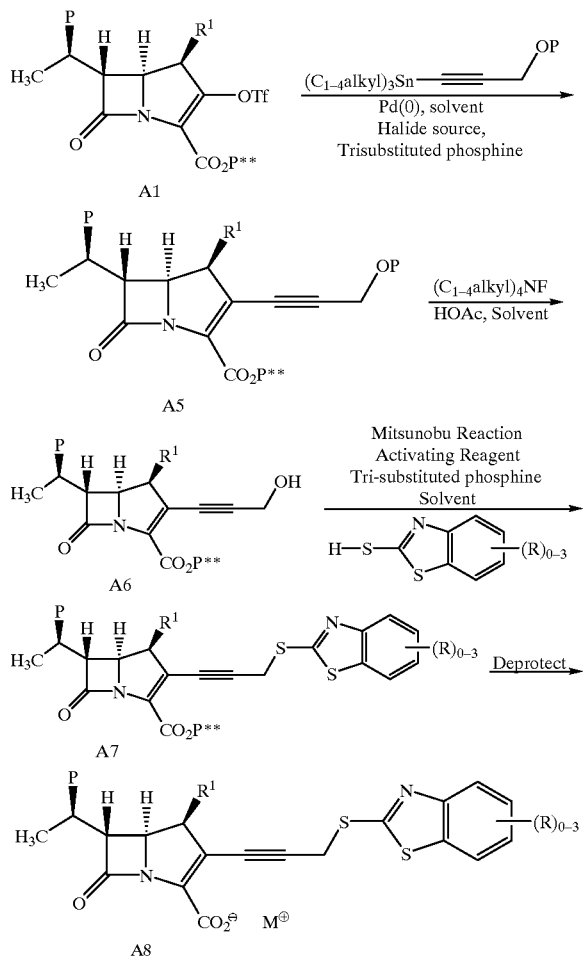

The methylene linked carbapenems are prepared as shown in Flow Sheet C in which intermediate A9 is reacted with the 2-mercaptobenzothiazole compound under Mitsunobu conditions to produce A10. Removing any protecting groups which are present affords the desired final product A11.

FLOW SHEET C

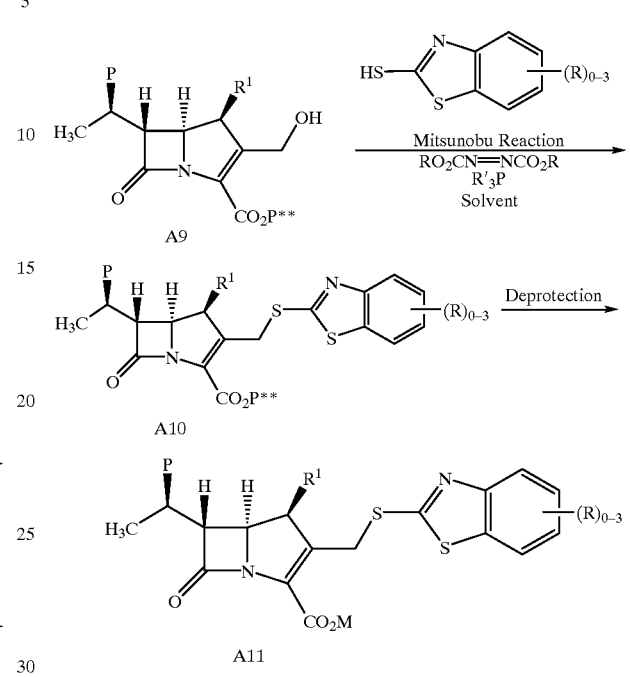

Flow Sheet D describes the synthesis of mercaptobenzothiazoyl carbapenem that possess a charged group Q, as previously defined. Typically, the intermediates A3, A7 and A10 from Flow Sheets A, B and C possess an R group, as previously defined, which allows for the introduction of Q. Thus, generalized intermediate A12 is selectively deprotected to produce alcohol A13, which in term is activated for displacement with Q by conversion to intermediate A14. A14 is reacted with Q to form the quaternary ammonium intermediate A15. Removal of any protecting groups affords the final product A16.

FLOW SHEET D

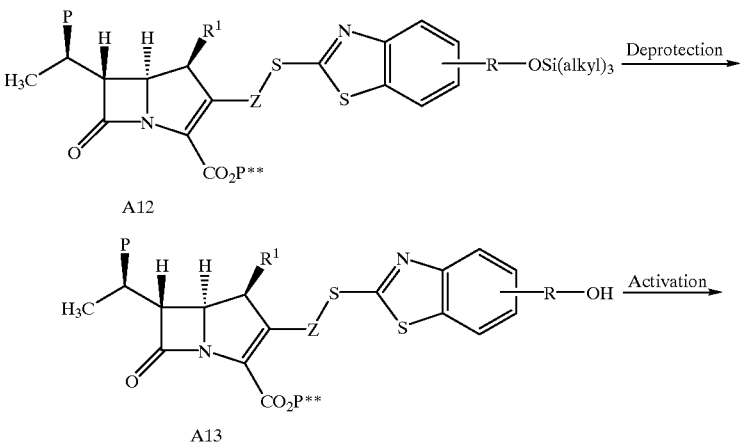

-continued

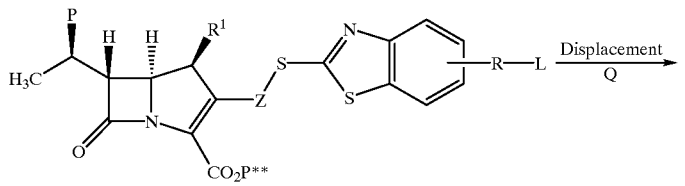

A14

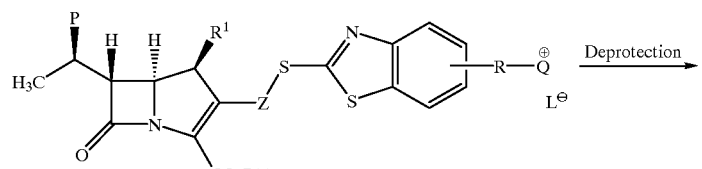

A15

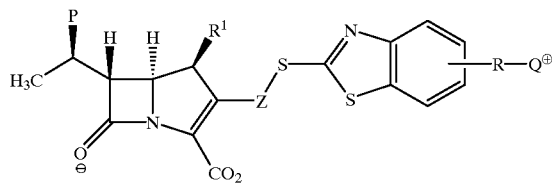

A16

With reference to the flow sheets above, P, $R^1$, R, and M, are as defined with respect to the compounds of formula I, except that $M^+$ may be a metal cation, e.g., $Na^+$. See Dykstra et al., *Tet. Lett.*, 1998, 39, pg. 1865.

P** represents a carboxyl protecting group.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxy-ethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

5-(2-HYDROXYETHYL)-2-THIOXO-2,3-DIHYDROBENZOTHIAZOLE

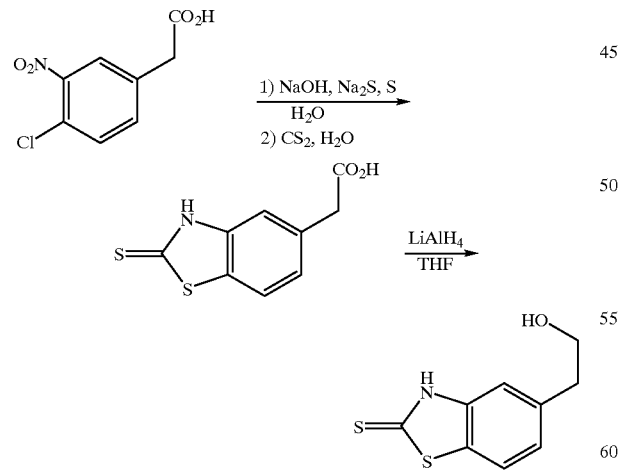

Step 1: 5-Carboxymethyl-2-thioxo-2,3-dihydrobenzothiazole

A solution of 4-chloro-3-nitro-phenylacetic acid (25.0 g, 0.116 mol) in 1N aqueous NaOH (143 mL, 0.143 mol) was added to preformed polysulfide solution (from 72.42 g, 0.301 mol of $Na_2S.9H_2O$, 26.87 g, 0.837 mol of S, and 74 mL of $H_2O$) at 50° C. The resulting mixture was mechanically stirred as the temperature of the oil bath was gradually increased to 115° C. over 10 min. The mixture was stirred at that temperature for two hours then allowed to cool to room temperature over two hours. Carbon disulfide (13.9 mL, 0.231 mol) was added and the reaction flask was placed in a 50° C. oil bath. The reaction mixture was stirred at that temperature for 18 hours then cooled in an ice bath, stirred, and acidified by cautious addition of glacial acetic acid (50 mL). The mixture was filtered and the filter cake was washed with water. The solid was stirred with sodium carbonate (30.7 g, 0.29 mol) in water then filtered to remove sulfur. The filtrate was cooled in an ice-bath and gradually acidified to pH 3.3 by addition of 6N HCl (100 mL). The precipitate was collected, washed with ice-cold water (100 mL) and dried in vacuo to a pale brown solid (21.5 g, 82%). This crude product was recrystallized from ethanol to afford 5-carboxymethyl-2-thioxo-2,3-dihydrobenzothiazole as a pale brown solid (14.2 g).

$^1$H NMR (DMSO-$d_6$, 500 MHz) δ3.65 (s, $CH_2$), 7.16 (d, H-6), 7.21 (s, H-4), and 7.58 (d, H-7).

$^{13}$C NMR (DMSO-$d_6$, 125.7 MHz) δ40.3 ($CH_2$), 113.2 (C-4), 121.4 (C-7), 125.7 (C-6), 127.6 (C-7a), 134.5 (C-5), 141.3 (C-3a), 172.4 ($CO_2$), and 190.1 (C-2).

Step 2; 5-(2-Hydroxyethyl)-2-thioxo-2,3-dihydrobenzothiazole

A solution of lithium aluminum hydride (65 mL of a 1M tetrahydrofuran solution, 0.065 mol) was added dropwise over 15 min to a mechanically stirred and refluxing solution of 5-carboxymethyl-2-thioxo-2,3-dihydrobenzothiazole (11.27 g, 0.050 mol) in anhydrous tetrahydrofuran (150 mL). The resulting mixture was stirred at reflux for 90 min then cooled in an ice-bath and cautiously treated with 2N hydrochloric acid (250 mL). The resulting mixture was diluted with water (250 mL) and extracted three times with ethyl acetate (250, 250, and 150 mL). The combined extracts were washed with brine (2×200 mL), dried over magnesium sulfate, filtered and concentrated in vacuo to approximately 140 mL volume. Some solid was present at this point. The mixture was diluted with ether (100 mL) and filtered. The filter cake was washed with ether and dried in vacuo to afford 5-(2-hydroxyethyl)-2-thioxo-2,3-dihydrobenzothiazole (8.58 g) as pale tan crystals.

$^1$H NMR (DMSO-$d_6$, 500 MHz) δ2.76 (t, ArC$\underline{H_2}$CH$_2$OH), 3.59 (t, ArCH$_2$C$\underline{H_2}$OH), 7.14 (d, H-6), 7.15 (s, $\underline{H}$-4), and 7.55 (d, H-7).

$^{13}$C NMR (DMSO-$d_6$, 125.7 MHz) δ38.7, 61.9, 112.7, 121.3, 125.3, 126.8, 139.3, 141.3, and 189.9.

PREPARATIVE EXAMPLE 2

5-ACETYL-2-THIOXO-2,3-DIHYDROBENZOTHIAZOLE

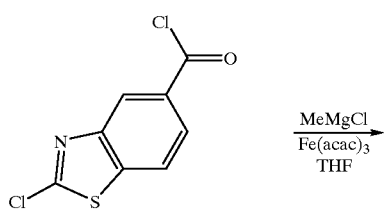

-continued

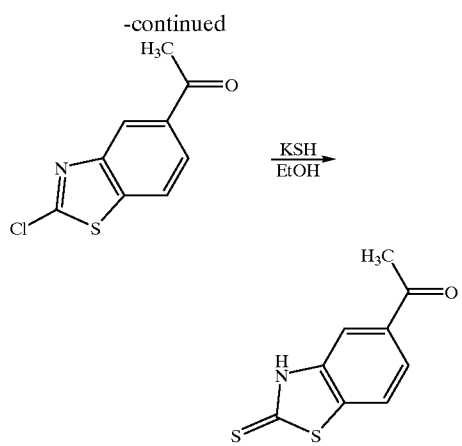

Step 1: 5-Acetyl-2-chlorobenzothiazole

A solution of 2-chloro-5-(chlorocarbonyl)benzothiazole (321 mg, 1.38 mmol, prepared according to U.S. Pat. No. 3,654,296) and ferric acetylacetonate (14.7 mg, 0.042 mmol) in anhydrous tetrahydrofuran (13.8 mL) was cooled in an ice-methanol bath (−20° C.), stirred under a nitrogen atmosphere, and treated dropwise over 5 minutes with 1M methyl magnesium chloride in tetrahydrofuran (1.38 mL). The resulting mixture was stirred at −15° C. for 15 minutes then at room temperature for 30 minutes. The mixture was treated with 2N hydrochloric acid (1.38 mL), diluted with water, and extracted with ethyl acetate. The extracts were washed with 5% aqueous sodium bicarbonate and brine, dried over magnesium sulfate, filtered, and evaporated in vacuo to white solid (299 mg). The crude product was purified by flash chromatography on silica gel (25 g, loaded as a dichloromethane solution and eluted with 2% ethyl acetate in dichlormethane) to afford 5-acetyl-2-chlorobenzothiazole (201 mg) as a white solid.

IR (KBr) 1674, 1599, 1482, 1419, 1358, 1285, 1256, 1207, 1091, 1060, 1020, 897, 818, and 650 cm$^{-1}$.

$^1$H NMR (CDCl$_3$, 500 MHz) δ2.68 (s, CH$_3$), 7.86 (d, H-7), 8.04 (dd, H-6), and 8.49 (d, H-4).

$^{13}$C NMR (CDCl$_3$, 125.7 MHz) δ26.7, 121.3, 123.2, 124.9, 136.0, 140.8, 150.9 and 197.0.

Step 2: 5-Acetyl-2-thioxo-2,3-dihydrobenzothiazole

A mixture of 5-acetyl-2-chlorobenzothiazole (137 mg, 0.65 mmol), potassium hydrogen sulfide (94 mg, 1.30 mmol) and ethanol (3.3 mL) in a capped flask was stirred in an oil bath at 80° C. for two hours. The mixture was cooled in ice, acidified with 1N hydrochloric acid (1.35 mL) and evaporated in vacuo. The residue was partitioned between water (25 mL) and ethyl acetate (50, 25 mL). The organic extracts were washed with brine, dried over magnesium sulfate, filtered and evaporated in vacuo to a solid (133 mg). This material was triturated with ether and dried to provide 5-acetyl-2-thioxo-2,3-dihydrobenzothiazole (110 mg) as a pale yellow solid.

IR (KBr) 1679, 1570, 1514, 1451, 1356, 1329, 1266, 1215, 1089, 1068, 1035, 876, 824, 730, 674, and 610 cm$^{-1}$.

$^1$H NMR (DMSO-d$_6$ 500 MHz) δ2.59 (s, CH$_3$), 7.72 (d, H-4), 7.82 (d, H-7), and 7.87 (dd, H-6).

$^{13}$C NMR (CDCl$_3$, 125.7 MHz) δ26.8, 111.0, 122.0, 124.2, 134.7, 135.6, 141.5, 190.6, and 196.9.

PREPARATIVE EXAMPLE 3

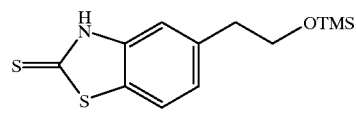

To a stirred solution of 300.0 mg (1.42 mmoles) of the carbinol obtained in preparative example 2, in 8.0 ml of sieve dried DMF, cooled to 0° C., is added imidazole (105 mg, 1.71 mmoles) and neat chlorotrimethylsilane (0.189 ml, 1.49 mmoles). The solution is stirred for 1 hr., diluted with ethyl acetate and washed with ice-water, 0.50 ml of 2.0N aq. HCl and saturated brine. The organic phase is dried over anhydrous sodium sulfate, filtered and conc. in vacuo to dryness. Purification by silica gel plate layer chormatography gives the product.

PREPARATIVE EXAMPLE 4

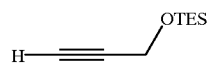

To a stirred solution of commercially available propargyl alcohol (5.0 g, 35.72 mmoles) in 50 ml of sieve dried DMF, cooled to 0° C., was added imidazole (668 mg, 9.83 mmoles) followed by neat triethylsilyl chloride (16.2 ml, 96.21 mmoles). The cooling bath was removed and the mixture was stirred at ambient temperature for 10 min. The resulting solution was diluted with ethyl acetate, washed with water-ice, 0.5M aq. sodium bicarbonate and saturated brine. The organic phase was dried over anhydrous sodium sulfate, filtered and concentrated in vacuo to give a colorless oil. Fractional distillation gave 3.03 g (51%) (b.p. 57° C.–61° C., 3.7 mm); of pure product as a colorless oil.

$^1$H NMR (CDCl$_3$) δ:0.65 (q, 6H), 0.95 (t, 9H), 2.43 (t, 1H), 4.35 (dd, 2H).

PREPARATIVE EXAMPLE 5

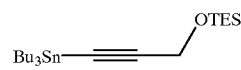

To a stirred solution of product obtained in preparative example 2 (3.03 g, 18.15 mmoles), in 30 ml of THF, cooled to −78° C., was added n-butyllithium (8.0 ml, 19.96 mmoles) dropwise over 30 min. The reaction was allowed to warmed to −20° C. and was stirred for 1 hour. Neat tri-n-butyltin chloride (5.89 ml, 21.78 mmoles) was then added dropwise over 30 min. The reaction mixture was warmed to 0° C. and stirred for 1 hr. The resulting dark solution was diluted with ethyl acetate, washed with water-ice and sat. brine. The organic phase was dried over anhydrous sodium sulfate, filtered and concentrated in vacuo to give a brown oil. Flash chromatography with 200–400 mesh florisil (100:1 florisil: product, eluent: 9:1 hexanes:dichloromethane) gave 6.12 g (74%) of the product as a colorless oil.

$^1$H NMR (CDCl3) δ: 0.64 (q, 6H), 0.91 (t, 6H), 1.02 (t, 18H), 1.31 (m, 6H), 1.72. (m, 6H), 4.34 (s, 2H).

EXAMPLE 1

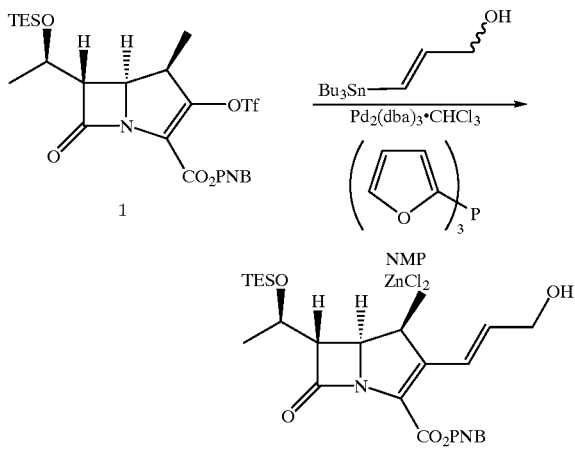

A mixture of 2-yl-carbapenem triflate 1 (200 mg, 0.329 mmoles), a 2:1 mixture of (E)-trans: (Z)-cis vinylstannanes (0.144 ml 0.493 mmoles), prepared as described in Jung, M. E.; Light, L. A. *Tetrahedron Lett.* 1982, 23, 3851, palladium dibenzylidineacetone chloroform complex (17 mg, 0.0165 mmoles) and tris-trifuryl phosphine (7.6 mg, 0.0329 mmoles) was combined and dissolved in 4.0 ml of N-methylpyrrolidinone, at ambient temperature. A 1.0 M etheral solution of zinc chloride (0.0329 ml, 0.0329 mmoles) was then added to the solution and the mixture was stirred for 6 hrs. The mixture was diluted with ethyl acetate, washed with water-ice and sat. brine. The organic phase was dried over anhydrous sodium sulfate, filtered and conc. in vacuo to give a brown oil. Silica gel plate layer chromatography (4×1000 microns, eluent: 1:1 ethyl acetate: hexanes) yielded 103 mg (60%) of the desired product as a colorless oil.

$^1$H NMR (CDCl$_3$) δ: 0.58 (m, 6H), 0.94 (t, 9H), 1.22 (d, 3H), 1.29 (d, 3H), 3.23 (dd, 1H), 3.37 (d, 1H), 4.19 (dd, 1H), 4.21 (m, 1H), 4.32 (dd,2H), 5.26–5.48 (q, 2H), 6.18 (dd, 1H), 7.27 (d, 1H), 7.68 (d, 2H), 8.22 (d, 2H).

EXAMPLE 2

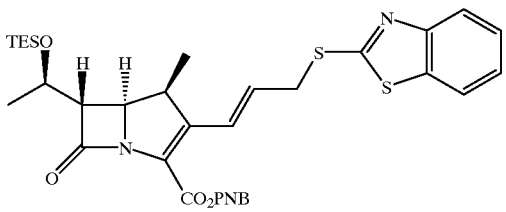

The carbinol (70 mg, 0.116 mmoles) obtained from example 1, along with commercially available 2-mercaptobenzothiazole (25 mg, 0.149 mmoles) and triphenylphosphine (39 mg, 0.149 mmoles) were combined in 2.0 ml of anhydrous THF and cooled to 0° C. Neat diisopropylazodicarboxylate (0.029 ml, 0.149 mmoles) was added and the mixture was stirred for 20 min. The resulting solution was concentrated in vacuo to give an orange oil. Purification by silica gel plate layer chromatography (1×1000 microns; eluent: 4:1 hexanes:ethyl acetate) gave 57 mg (71 %) of a yellow oil.

$^1$H NMR (CDCl$_3$) δ: 0.53 (q, 6H), 0.88 (t, 9H), 1.16 (d, 3H), 1.25 (d, 3H), 3.19 (dd, 1H), 3.31 (m, 1H), 4.13 (m, 4H), 5.24–5.47 (ABq, 2H), 6.17 (m, 1H), 7.28 (t, 1H), 7.38 (m, 2H), 7.65 (d, 2H), 7.44 (d, 1H), 7.77 (d, 1H), 7.86 (d, 1H), 8.19 (d, 2H).

EXAMPLE 3

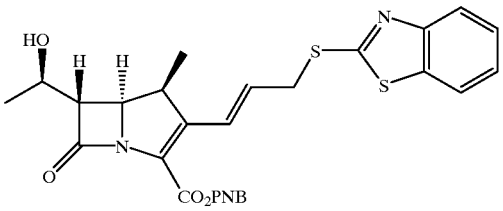

To a stirred solution of 170 mg (0.213 mmoles) of the product obtained in example 2, in 2.0 ml of anhydrous THF, cooled to 0° C., was added sequentially acetic acid (0.040 ml, 0.708 mmoles) and a 1.0 M THF solution of tetrabutylammonium fluoride (0.354 ml, 0.354 mmoles). The mixture was stirred for 1 hr., diluted with ethyl acetate, washed with water-ice, saturated aq. sodium bicarbonate and sat. brine. The organic phase was dried over anhydrous sodium sulfate, filtered and concentrated in vacuo to provide an orange residue. Purification by silica gel plate layer chromatography gives the product.

$^1$H NMR (CDCl$_3$) δ: 1.16 (d, 3H), 1.32 (d, 3H), 3.22 (dd, 1H), 3.36 (m, 1H), 4.13 (d, 2H), 4.15 (dd, 1H), 4.21 (m, 1H), 5.21–5.48 (ABq, 2H), 6.22 (m, 1H), 7.27 (t, 1H), 7.30 (m, 2H), 7.63 (d, 2H), 7.73 (d, 1H), 7.75 (d, 1H), 8.19 (d, 2H).

EXAMPLE 4

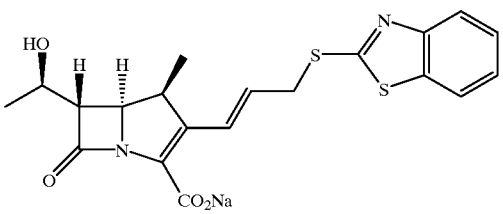

To a stirred solution of 31 mg (0.0562 mmoles) of the product obtained in example 3, in 1.5 ml of a 2:1 mixture of THF-H$_2$O, cooled to 0° C., was added 1.0 N aq. sodium bicarbonate (0.059 ml, 0.059 mmoles) and 5% Pt/C (3.1 mg) catalyst. The cooling bath was removed and the reaction mixture was stirred vigorously under a balloon of hydrogen, at ambient temperature for 6 hrs. The reaction mixture was filtered through celite, rinsed with 1:1 water: acetonitrile and concentrated in vacuo to give an orange residue. R verse phase silica gel plate layer chromatography (1×1000 microns, eluent: 3:1 H$_2$O: acetonitrile) gave after lyophilization 9.3 mg (37.8%) of desired product as a white solid.

$^1$H NMR (2:1 D$_2$O: CD$_3$CN) δ: 1.35 (d, 3H), 1.54 (d, 3H), 3.54 (dd, 1H), 3.60 (m, 1H), 4.37 (dd, 1H), 4.41 (d, 2H), 4.45 (m, 1H), 6.34 (m, 1H), 7.65 (d, 1H), 7.71 (t, 1H), 7.92 (t, 1H), 8.18 (d, 1H), 8.24 (d, 1H).

EXAMPLE 5

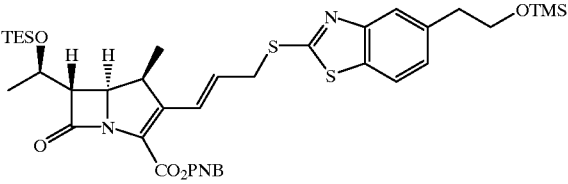

The carbinol (85 mg, 0.164 mmoles) obtained from example 1, along with (48 mg, 0.173 mmoles) of the product obtained from preparative example 2, and triphenylphosphine (45 mg, 0.173 mmoles) is combined in 2.0 ml of anhydrous THF and cooled to 0° C. Neat diisopropylazodicarboxylate (0.034 ml, 0.173 mmoles) is added and the

EXAMPLE 6

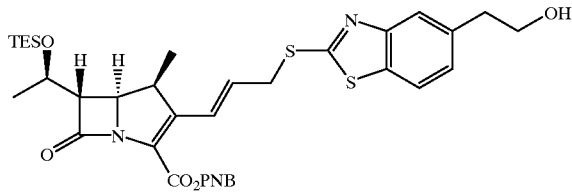

To a stirred solution of 95 mg (0.121 mmoles) of the product obtained in example 5, in 2.0 ml of anhydrous THF, cooled to 0° C., is added sequentially acetic acid (0.01 ml, 0.182 mmoles) and a 1.0 M THF solution of tetrabutylammonium fluoride (0.133 ml, 0.133 mmoles). The mixture is stirred for 1 hr., diluted with ethyl acetate, washed with water-ice, saturated aq. sodium bicarbonate and sat. brine. The organic phase is dried over anhydrous sodium sulfate, filtered and concentrated in vacuo to provide an orange residue. Purification by silica gel plate layer chromatography gives the product.

EXAMPLE 7

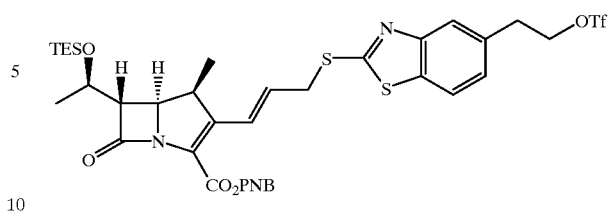

To a stirred solution of 75 mg (0.106 mmoles) of the product obtained in example 6, in 1.0 ml of anhydrous THF, cooled to −20° C., is added neat 2,6-lutidine (0.0130 ml, 0.111 mmoles) and the solution is stirred for 5 min. Neat triflic anhydride (0.019 ml, 0.116 mmoles) is then added and the mixture is stirred for 15 min. The reaction mixture is diluted with ethyl acetate, washed with water-ice, 0.050 ml of 2.0N aq. HCl and saturated brine. The organic phase is dried over anhydrous sodium sulfate, filtered and concentrated in vacuo to give the product which is used without purification.

EXAMPLE 8

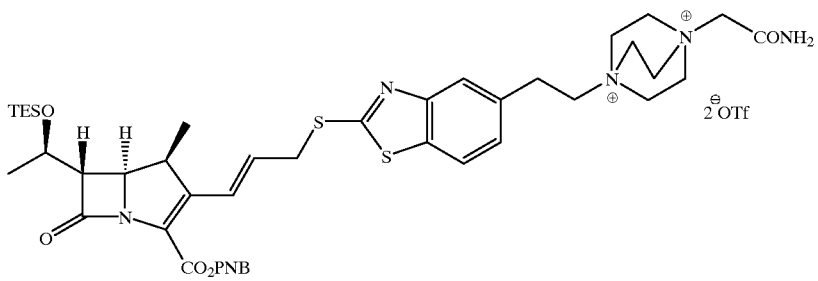

To a stirred solution of 75 mg (0.0890 mmoles) of freshly prepared product obtained from example 7, in 1.0 ml of sieve dried acetonitrile, at ambient temperature, is added 4-carbamoylmethyl-1,4-diazoniabicyclo-{2.2.2}-octyl triflate (28 mg, 0.0890 mmoles). The solution is stirred for 30 min., concentrated in vacuo to dryness and dissolved in 1.0 ml of acetone. The solution is diluted with 8.0 ml of diethyl ether to give a milky suspension which is centrifuged and dried to give the product.

EXAMPLE 9

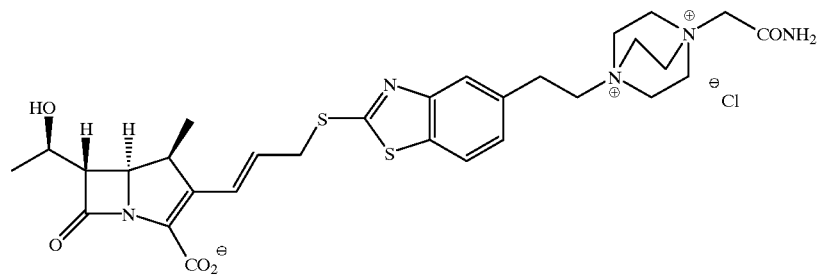

To a stirred solution of 60 mg (0.0531 mmoles) of the product obtained in example 8, in a 2:1 mixture of THF-H$_2$O, cooled to 0° C., is added 1.0 N aq. HCl (0.0531 ml, 0.0531 mmoles). The cooling bath is removed and the reaction is stirred at ambient temperature for 1.5 hrs. The mixture is cooled to 0° C. and neutralized with 1.0N aq. sodium bicarbonate (0.0531 ml, 0.0531 mmoles) and charged with 5% Pt/C (6.0 mg) catalyst. The suspension is stirred vigorously, under a balloon of hydrogen, at ambient temperature for 30 min. The mixture is filtered through celite, washed with ethyl acetate and concentrated in vacuo to dryness. The resulting residue is dissolved in 2.0 ml of deionized water and is passed through a column containing Macro prep ion exchange resin and eluted with a 5% aq. brine solution. The resulting solution is subsequently desalted using amberchrom CG-161 resin to give after lyophilization the product.

EXAMPLE 10

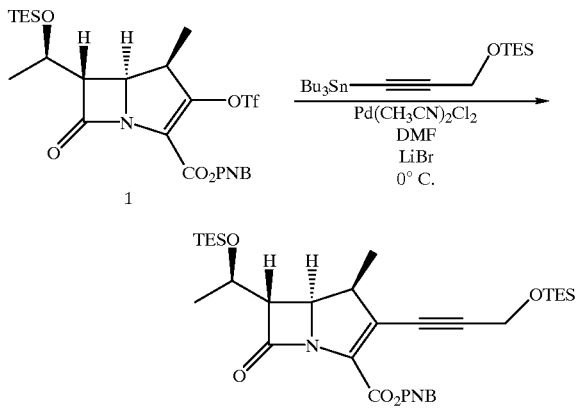

To a stirred solution of carbapenem 2-yl-triflate 1 (100 mg, 0.164 mmoles) and propargylstannane (112 mg, 0.246 mmoles) obtained in preparative example 19, in 2 mL of anhydrous DMF, at 0° C., was added lithium bromide (28 mg, 0.328 mmoles) and bis-acetonitrilepalladium (II) chloride (2.1 mg, 0.0082 mmoles). The reaction mixture was stirred for 1 hr., diluted with ethyl acetate and washed with water-ice and saturated brine. The organic phase was dried over anhydrous sodium sulfate, filtered and concentrated in vacuo to give an orange oil. Silica gel plate layer chromatography (2×1000 microns; eluent: 4:1 hexane ethyl acetate) gave 70 mg (68%) of the desired product as a pale yellow oil.

$^1$H NMR (CDCl$_3$) δ: 0.59 (m, 12H), 0.73 (m, 18H), 1.24 (d, 3H), 1.26 (d, 3H), 3.18 (m, 1H), 3.20 (dd, 1H), 4.12 (d, 1H), 4.25 (dd, 1H), 4.53 (s, 2H), 5.28–5.49 (q, 2H), 7.65 (d, 2H), 8.21 (d, 2H).

EXAMPLE 11

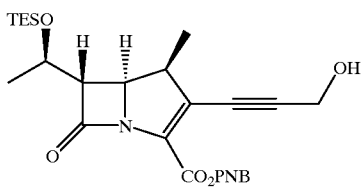

To a stirred solution of 77 mg (0.122 mmoles) of the product obtained in example 10, in 1.0 ml of anhydrous THF, at 0° C., was added sequentially acetic acid (11 ml, 0.183 mmoles) and a 1.0 M THF solution of tetra-butylammonium fluoride (0.122 ml, 0.122 mmoles). The mixture was stirred for 1 hr., diluted with ethyl acetate, washed with water, saturated aq. sodium bicarbonate and saturated brine. The organic phase was dried over sodium sulfate, filtered and concentrated in vacuo to give a yellow solid. Silica gel plate layer chromatography (1×1000 microns; eluent:1:1 hexanes:ethyl acetate) gave 33 mg (53%) of a yellow crystalline solid.

$^1$H NMR (CDCl$_3$) δ: 0.57 (q, 6H), 0.90 (t, 9H), 1.22 (t, 6H), 1.74 (t, 1H), 3.16 (m, 1H), 3.23 (dd, 1H), 4.23–4.32 (m, 2H), 4.48 (d, 2H), 5.26–5.48 (q, 2H), 7.64 (d, 2H), 8.21 (d, 2H).

EXAMPLE 12

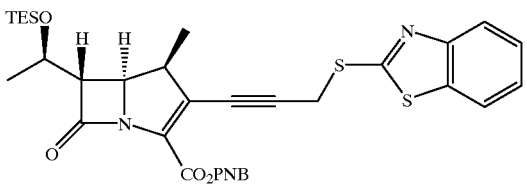

Using the procedure described in example 5, the carbinol (66 mg, 0.128 mmoles) obtained from example 1, along with 2-mercaptobenzothiazole (24 mg, 0.141 mmoles), and triphenylphosphine (37 mg, 0.141 mmoles) was combined in 2.0 ml of anhydrous THF and treated with neat diisopropyla-zodicarboxylate (0.028 ml, 0.141 mmoles). The resulting solution was concentrated in vacuo to give an orange oil. Silca gel plate layer chromatography (1×1000 microns; eluent: 4:1 hexanes:ethyl acetate) gave 74 mg (88%) of a yellow solid.

$^1$H NMR (CDCl$_3$) δ: 0.56 (q, 6H), 0.89 (t, 9H), 1.13 (d, 3H), 1.21 (d, 3H), 3.09 (m, 1H), 3.28 (dd, 1H), 4.18 (m, 2H), 4.43 (s, 2H), 5.21–5.45 (ABq, 2H), 7.28 (t, 1H), 7.42 (t, 1H), 7.56 (d, 2H), 7.74 (d, 1H), 7.85 (d, 1H), 8.19 (d, 2H).

EXAMPLE 13

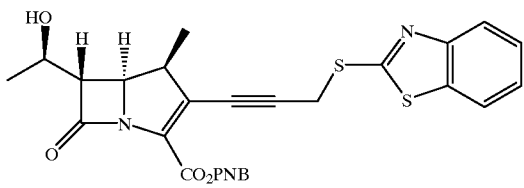

To a stirred solution of 75 mg (0.113 mmoles) of the product obtained in example 12, in 2.0 ml of a 3:1 mixture of THF-H$_2$O, cooled to 0° C., was added 1.0N aq. HCl (0.0565 ml, 0.0567 mmoles). The mixture is stirred for 3 hrs., diluted with ethyl acetate, washed with water-ice, saturated aq. sodium bicarbonate and sat. brine. The organic phase was dried over anhydrous sodium sulfate, filtered and concentrated in vacuo to provide an orange residue. Purification by silica gel plate layer chromatography (1×1000 microns; eluent: 3:2 ethyl acetate:hexanes) gave 42 mg (68%) of the desired product as a tan solid.

$^1$H NMR (CDCl$_3$) δ: 1.14 (d, 3H), 1.29 (d, 3H), 3.14 (m, 1H), 3.30 (dd, 1H), 4.24 (m, 2H), 4.33 (s, 2H), 5.20–5.42 (ABq, 2H), 7.30 (t, 1H), 7.39 (t, 1H), 7.56 (d, 2H), 7.74 (d, 1H), 7.54 (d, 1H), 7.88 (d, 1H), 8.15 (d, 2H).

EXAMPLE 14

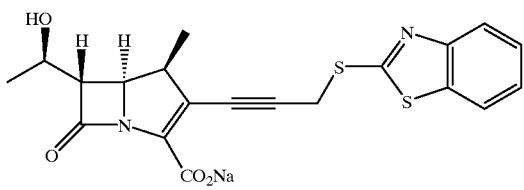

To a stirred solution of 23 mg (0.0419 mmoles) of the product obtained in example 3, in 1.5 ml of a 2:1:1 mixture of THF-H$_2$O: EtOH, cooled to 0° C., was added 1.0 N aq. sodium bicarbonate (0.046 ml, 0.046 mmoles) and 5% Pt/C (4.6 mg) catalyst. The cooling bath was removed and the reaction mixture was stirred vigorously under a balloon of hydrogen, at ambient temperature for 45min. The reaction mixture was filtered through celite, rinsed with 1:1 water: acetonitrile and concentrated in vacuo to give an orange residue. Reverse phase silica gel plate layer chromatography (1×1000 microns, eluent: 3:1 H$_2$O:acetonitrile) gave after lyophilization 6.9 mg (37.8%) of desired product as a white solid.

$^1$H NMR (2:1 D$_2$O: CD$_3$CN) δ: 1.37 (d, 3H), 1.59 (d, 3H), 3.40 (m, 1H), 3.73 (dd, 1H), 4.55 (m, 2H), 4.73 (d, 2H), 7.85 (t, 1H), 7.87 (t, 1H), 7.95 (t, 1H), 8.34 (d, 1H), 8.39 (d, 1H).

EXAMPLE 15

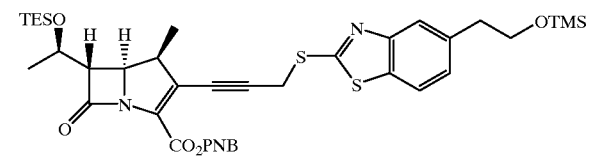

Using the procedure described in example 5, the carbinol (79 mg, 0.153 mmoles) obtained from example 1, along with 52 mg (0.183 mmoles) of the product obtained from preparative example 2, and triphenylphosphine (48 mg, 0.183 mmoles) is combined in 2.0 ml of anhydrous THF and cooled to 0° C. Neat diisopropylazodicarboxylate (0.036 ml, 0.183 mmoles) is added and the mixture is stirred for 20 min. The resulting solution is concentrated in vacuo and the residue purified by silca gel plate layer chromatography to give the product.

EXAMPLE 16

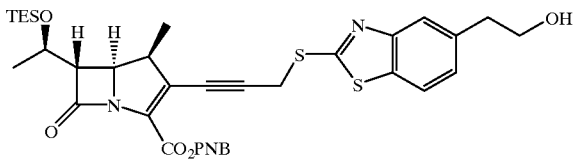

Using the procedure described in example 13, a stirred solution of 59 mg (0.075 mmoles) of the product obtained in example 15, in 1.5 ml of a 3:1 mixture of THF-H$_2$O cooled to 0° C. is added 1.0N aq. HCl (0.0188 ml, 0.0188 mmoles). The mixture is stirred for 30 min., diluted with ethyl acetate, washed with water-ice, saturated aq. sodium bicarbonate and sat. brine. The organic phase is dried over anhydrous sodium sulfate, filtered and concentrated in vacuo to provide an orange residue. Purification by silica gel plate layer chromatography gives the product.

EXAMPLE 17

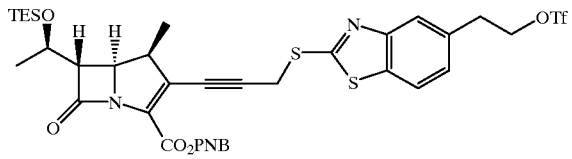

Using the procedure described in example 7, a stirred solution of 92 mg (0.129 mmoles) of the product obtained in example 6, in 1.0 ml of anhydrous THF, cooled to −20° C., is added neat 2,6-lutidine (0.0160 ml, 0.136 mmoles) and the solution is stirred for 5 min. Neat triflic anhydride (0.022 ml, 0.129 mmoles) is then added and the mixture was stirred for 15 min. The obtained product is used without purification.

EXAMPLE 18

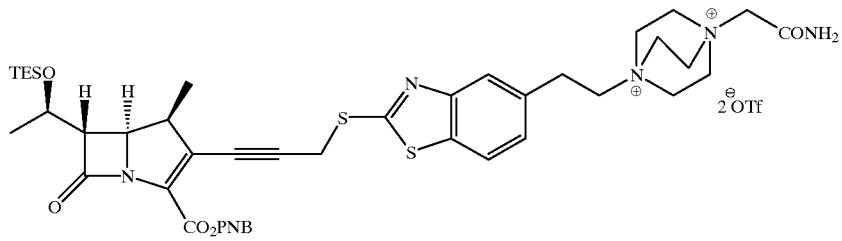

Using the procedure described in example 8, a stirred solution of 63 mg (0.0740 mmoles) of freshly prepared product obtained from example 17, in 1.0 ml of sieve dried acetonitrile, at ambient temperature, is added 4-carbamoylmethyl-1,4-diazoniabicyclo-{2.2.2}-octyl triflate (24 mg, 0.0740 mmoles). Precipitated from an acetone/ether solution gives the product.

EXAMPLE 19

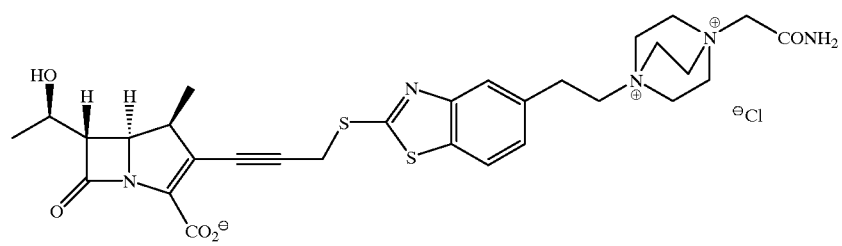

Using the procedure described in example 9, a stirred solution of 54 mg (0.0478 mmoles) of the product obtained in example 8, in a 2:1 mixture of THF-$H_2O$, cooled to 0° C., is added 1.0 N aq. HCl (0.0478 ml, 0.0478 mmoles). The mixture is hydrogenated using 5% Pt/C (4.7 mg), treated with Macro prep ion exchange resin and desalted using amberchrom CG-161 resin to give after lyophilization the product.

EXAMPLE 20

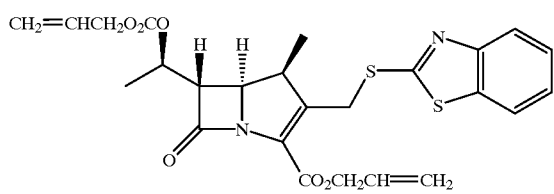

To a stirred solution of a mixture of 2-mercaptobezothiazole (0.0299 g, 0.179 mmoles), the bis-allyl protected carbinol (0.0593 g, 0.162mmoles), and triphenylphosphine (0.0511 g, 0.195 mmoles) in 1 mL dry, distilled THF at 0° C. under a $N_2$ atmosphere was added neat diisopropylazodicarboxylate (0.0384 mL, 0.195 mmoles). The reaction was stirred for 15 minutes, and concentrated in vacuo. The residue was purified by plate layer chomatography eluting $CH_2Cl_2$-EtOAc (50:1) to afford the coupled product (0.0795 g, 95% yield).

IR($CH_2Cl_2$): 1781, 1747, 1720 $cm^{-1}$;

$^1$H NMR (CDCl$_3$) δ: 1.25 (d, 3H), 1.44 (d, 3H), 3.34 (m, 1H), 3.42 (dd, 1H), 4.15 (dd, 1H), 4.22 (d, 1H), 5.0 (d, 1H), 7.31–7.86 (m, 4H);

UV:λmax(dioxane) 322, 294, 285 nm.

EXAMPLE 21

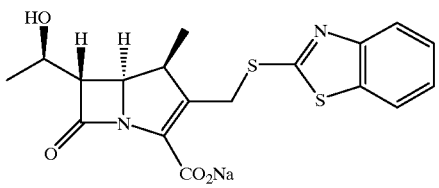

To a solution of carbapenem (0.0693 g, 0.135 mmoles), prepared in the previous example, in 1:1 $CH_2Cl_2$/EtOAc (4 mL) was added under $N_2$, 2-ethylhexanoic acid (0.01 mL, 0.074 mmoles), 0.5 M solution of sodium-2-ethyl-hexanoate (0.020 mL, 0.148 mmoles), triphenylphosphine (0.0212 g, 0.081 mmoles), and Pd(PPh$_3$)$_4$ (0.0311 g, 0.027 mmoles). The reaction was stirred at ambient temperature for 15 min. and then stirred at 0° C. for another 60 min. The product was precipitated out of solution with the addition of $Et_2O$. The resulting mixture was centrifuged and the supernatant discarded. The product was triturated with additional $Et_2O$ and dried in vacuo. The crude material was purified by reverse phase plate layer chromatography with 4:1$H_2O$—$CH_3CN$. The desired product was eluted off the silica gel with 4:1 $CH_3CN$—$H_2O$. Lyophilization gave the final compound (0.0106 g, 19% yield).

$^1$H NMR (5:1 $D_2O$/$CD_3CN$) δ: 1.28 (d, 3H), 1.37 (d, 3H), 3.48 (m, 1H), 3.51 (dd, 1H), 4.09 (d, 1H), 4.22 (dd, 1H), 4.31 (m, 1H), 5.18 (d, 1H), 7.55–8.11 (m, 4H);

UV:λmax(water) 300 sh, 282 nm.

EXAMPLE 22

Utilizing the procedure outlined in Example 20, 68.7 mg(0.188 mmoles) of carbapenem carbinol and 67.3 mg (0.207 mmoles) of triethylsilyl protected derivative of preparative example 1 in 1 mL of dry THF at 0° C. for 5 minutes gave after purification the carbapenem adduct depicted above.

$^1$H NMR (CDCl$_3$) δ: 1.25 (d, 3H), 1.44 (d, 3H), 2.95 (t, 2H), 3.34 (m, 1H), 3.41 (dd, 1H), 3.85 (t, 2H), 4.15 (dd, 1H), 4.24 (d, 1H), 5.0 (d, 1H), 7.12–7.69 (m, 3H).

EXAMPLE 23

To a stirred solution of 125.7 mg (0.187 mmoles) of carbapenem derivative prepared in the previous example in 2 mL of THF at 0° C. was added sequentially 21.8 μL (0.374 mmoles) of glacial acetic acid and then 206 μL of a 1M solution of tetrabutylammonium fluoride in THF. The mixture was stirred further for 30 minutes and then partitioned between ethyl acetate/ice/saturated sodium bicarbonate solution and the organic phase was separated, washed with brine, dried over anhydrous sodium sulfate, filtered, and evaporated. The residue was purified by PLC, [one development CH$_2$Cl$_2$-EtOAc(4:1)] to give 78.9 mg of alcohol.

IR(CH$_2$Cl$_2$): 3611, 1781, 1748, 1719 cm$^{-1}$;

$^1$H NMR (CDCl$_3$) δ: 1.23 (d, 3H), 1.41 (d, 3H), 2.97 (t, 2H), 3.32 (m, 1H), 3.39 (dd, 1H), 3.9 (t, 2H), 4.13 (dd, 1H), 4.19 (d, 1H), 4.97 (d, 1H), 7.17–7.69 (m, 3H).

UV: λmax(dioxane) 311, 295 nm.

EXAMPLE 24

To a stirred solution of 76.2 mg (0.137 mmoles) of carbapenem derivative prepared in the previous example and 27.2 μL (0.341 mmoles) of N-methyl-imidazole in 1 mL of CH$_2$Cl$_2$ at ice-salt water bath temperatures was added 28.7 μL (0.171 mmoles) of neat triflic anhydride. The mixture was stirred further for one hour and then partitioned between methylene chloride and water. The organic phase was separated, dried over anhydrous sodium sulfate, filtered, evaporated and dried in vacuo to give 100 mg of residue. The product in methylene chloride was precipitated by the addition of diethyl ether; dried in vacuo to give 66.9 mg (64%).

$^1$H NMR (CDCl$_3$) δ: 1.22 (d, 3H), 1.40 (d, 3H),3.29 (m, 2H), 3.32 (m, 1H), 3.42 (dd, 1H), 3.88 (s, 3H), 4.04 (d, 1H), 4.16 (dd, 1H), 5.01 (d, 1H), 7.04–9.09 (m, 6H).

EXAMPLE 25

Utilizing the procedure outlined in Example 21, 66.9 (0.0867 mmoles) of carbapenem derivative prepared in the previous example in 2 mL of 1:1 CH$_2$Cl2/EtOAc gave after workup and purification by reverse phase plate layer chromatography with 3:1H$_2$O—CH$_3$CN gave 15.1 mg (35%) of carbapenem product depicted above.

IR(nujol): 1752, 1590 cm$^{-1}$;

$^1$H NMR (5:1 D$_2$O/CD$_3$CN) δ: 1.28 (d, 3H), 1.37 (d, 3H),3.43 (t, 2H), 3.47 (m, 1H), 3.51 (dd, 1H), 3.89 (s, 3H), 4.06 (d, 1H), 4.22 (dd, 1H), 4.32 (m, 1H), 4.65 (t, 2H), 5.19 (d, 1H), 7.31–8.59 (m, 6H).

UV: λmax(water) 305 sh, 282 nm. 20248

What is claimed is:

1. A compound represented by formula I:

or a pharmaceutically acceptable salt thereof, wherein:

R$^1$ represents H or methyl;

CO$_2$M represents a carboxylic acid, or a carboxylate anion, wherein when CO$_2$M is a carboxylate anion it is balanced by a positively charged R group;

P represents hydrogen, hydroxyl, or F;

Z represents trans-ethenediyl or ethynediyl or a bond;

each R is independently selected from: —R*; —Q; A—(CH$_2$)$_n$—Q, wherein A is O, S, or CH$_2$, and n is 0–3; hydrogen; halo; —CN; —NO$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^h$: —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups; with the proviso that the positively charged moiety or moieties contained in one or more R groups be limited to 1–2 positive charges, balanced by a carboxylate anion and if needed a negatively charged counterion;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{3-7}$ cycloalkyl, unsubstituted or substituted with one to four R$^d$ groups;

or $R^a$ and $R^b$ taken together with any intervening atoms represent a 4–6 membered saturated ring optionally interrupted by one to three of O, S, $NR^c$, with $R^c$ as defined above, wherein cyclic peroxides are not formed, or —C(O)—, said ring being unsubstituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, wherein cyclic peroxides are not formed, or —C(O)—, said ring being unsubstituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2Rf$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —$R^*$ or —Q;

$R^e$, $R^f$ and $R^g$ represent hydrogen; —$R^*$; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, wherein cyclic peroxides are not formed, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_{3-6}$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$, wherein cyclic peroxides are not formed;

Q is selected from the group consisting of:

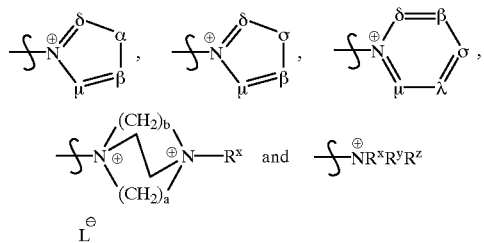

wherein:

a and b are 1, 2 or 3;

L– is a pharmaceutically acceptable counterion;

α represents O, S, or $NR^s$;

β, δ, λ, μ and σ represent $CR^t$, N or $N^+R^s$, provided that no more than one of β, δ, λ μ and σ is $N^+R^s$ $R^*$— is selected from the group consisting of:

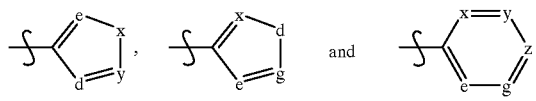

wherein:

d represents O, S, or $NR^k$ e, g, x, y and z represent $CR_m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR''R^o$; —$OR''$; —$SR''$; —$CONR''R^o$; —$COOR^h$; —$SOR''$; —$SO_2R''$; —$SO_2NR''R^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R''$ and $R^o$ represent hydrogen, phenyl; —$C_{1-6}$ straight- or branched-chain alkyl, unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR''R^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one to three of O, S, $NR^w$ or —C(O)—, wherein cyclic peroxides are not formed, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

Rx represents hydrogen or a $C_{1-8}$ straight- or branched-chain alkyl, optionally interrupted by one or two of O, S, SO, $SO_2$, $NR^w$, $N^+R^hR^w$, wherein cyclic peroxides are not formed, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$h)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight or branched-chain alkyl groups, said alkyl groups being unsubstituted or substituted with one to four R$^i$ groups;

R$^y$ and R$^z$ represent hydrogen; phenyl; —C$_{1-6}$ straight or branched chain alkyl, unsubstituted or substituted with one to four R$^i$ groups, and optionally interrupted by O, S, NR$^w$, N$^+$R$^h$R$^w$, or —C(O)—;

or R$^x$ and R$^y$ together with any intervening atoms represent a 4–6 membered saturated ring optionally interrupted by O, S, SO$_2$, NR$^w$, N$^+$R$^h$R$^w$ or —C(O), unsubstituted or substituted with 1–4 R$^i$ groups, and when R$^x$ and R$^y$ together represent a 4–6 membered ring as defined above, R$^z$ is as defined above or R$^z$ represents an additional saturated 4–6 membered heterocyclic ring fused or bridged between the nitrogen atom of the ring represented by R$^x$ and R$^y$ taken together and a carbon atom therein, optionally interrupted by O, S, NR$^w$ or —C(O)—, said rings being unsubstituted or substituted with one to four R$^i$ groups.

2. A compound in accordance with claim 1 wherein CO$_2$M represents a carboxylate anion.

3. A compound in accordance with claim 1 wherein one R represents a group which contains a positively charged moiety, and the remaining R groups are selected from hydrogen and C$_{1-6}$ straight or branched chain alkyl, unsubstituted or substituted with one to four R$^d$ groups.

4. A compound in accordance with claim 3 wherein one R represents a group containing a positively charged moiety and the remaining R groups are hydrogen.

5. A compound in accordance with claim 1 wherein the R groups contain from 1–2 positive groups.

6. A compound in accordance with claim 5 wherein the R groups contain 1–2 positive charges, balanced by a carboxylate anion and a pharmaceutically acceptable anion.

7. A compound in accordance with claim 1 wherein one R group represents a —C$_{1-6}$ straight or branched chain alkyl group, substituted with one to four R$^d$ groups, wherein one R$^d$ group represents —R* or Q.

8. A compound in accordance with claim 1 wherein Q is selected from the group consisting of:

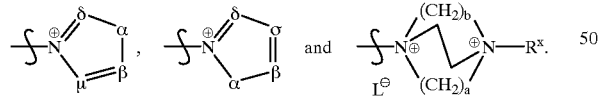

9. A compound in accordance with claim 8 wherein Q represents:

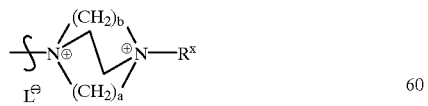

L$^-$, a and b are as originally defined, and R$^x$ represents a member selected from the group consisting of: hydrogen or a C$_{1-8}$ straight- or branched-chain alkyl, optionally interrupted or terminated by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, OC—(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl, or heteroaryl, said phenyl and heteroaryl being optionally substituted with from one to four R$^i$ groups or with one to two C$_{1-3}$ straight- or branched-chain alkyl groups, said alkyl groups being unsubstituted or substituted with one to four R$^i$ groups, and R$^h$, R$^i$ and R$^w$ are as originally defined.

10. A compound in accordance with claim 1 wherein Q represents —N$^+$R$^x$R$^y$R$^z$, wherein R$^x$, R$^y$ and R$^z$ are as originally defined.

11. A compound in accordance with claim 1 wherein one R* group is present and is selected from:

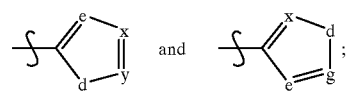

d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

12. A compound in accordance with claim 1 wherein:

CO$_2$M represents a carboxylate anion;

one R group which is attached to the 2-mercaptobenzothiazole platform contains at least one positively charged moiety, and the remaining R groups are selected from hydrogen and C$_{1-6}$ straight or branched chain alkyl, unsubstituted or substituted with one to four R$^d$ groups;

R$^d$ is as originally defined;

R$^h$ represents hydrogen or a C$_{1-6}$ straight or branched chain alkyl group;

Q is selected from the group consisting of:

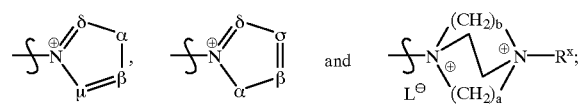

wherein L$^-$ is as originally defined; a and b represent 2, and R$^x$ represents a member selected from the group consisting of: hydrogen or a C$_{1-8}$ straight- or branched-chain alkyl, optionally interrupted or terminated by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl, or heteroaryl, said phenyl and heteroaryl being optionally substituted with from one to four R$^i$ groups or with one to two C$_{1-3}$ straight- or branched-chain alkyl groups, said alkyl groups being unsubstituted or substituted with one to four R$^i$ groups;

R* is selected from:

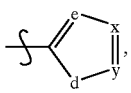 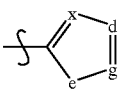

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

13. A compound in accordance with claim 1 wherein R is A—$(CH_2)_n$—Q, wherein A is O, S, or $CH_2$ and n is 0–3 and Q is as originally defined.

14. A compound in accordance with claim 1 wherein Z is trans-CH=CH.

15. A compound in accordance with claim 1 wherein Z is —C≡C—.

16. A compound in accordance with claim 1 wherein Z is absent.

17. A compound in accordance with claim 1 represent by formula Ia:

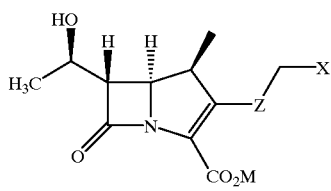

wherein X is:

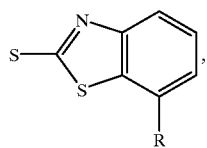

2

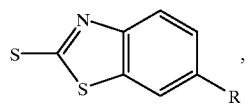

3

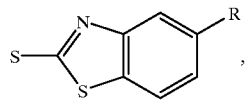

4

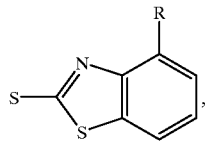

5

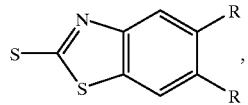

6

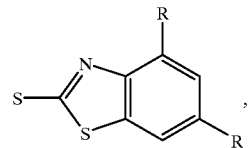

7

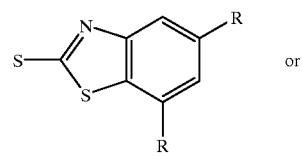

or

8

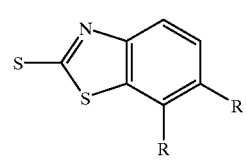

9 wherein:
Z is as originally described;
$CO_2M$ represents a carboxylate anion;
R group may contain a positively charged moiety;
Rd is as originally defined;
$R^h$ represents hydrogen or a $C_{1-6}$ straight or branched chain alkyl group;
Q is selected from the group consisting of:

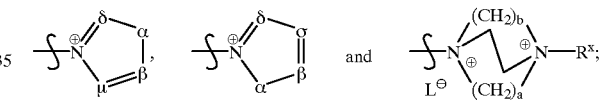

wherein $L^-$, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;
R* is selected from:

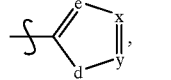 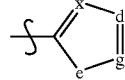

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

18. A compound in accordance with claim 17 wherein X is 4, 6 or 8 and R contains a positively charged moiety selected from the group consisting of: —R*, Q, A—$(CH_2)_n$ —Q, and a $C_{1-6}$ straight or branched alkyl chain substituted with one $R^d$ group, wherein A is as originally described $R^d$ is independently selected —R* or Q;

Q is selected from the group consisting of:

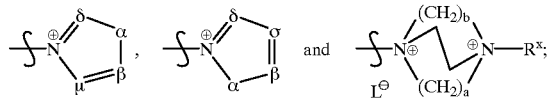

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2 R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O) NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

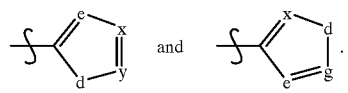

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

19. A compound in accordance with claim 17 wherein X is 4.

20. A compound in accordance with claim 17 wherein
X is 3, 7, or 9 and at least one R contains a positively charged moiety selected from the group consisting of: —R*, Q, A—$(CH_2)_n$—Q, and a $C_{1-6}$ straight or branched alkyl chain substituted with one $R^d$ group, wherein A is as originally described $R^d$ is independently selected —R* or Q;

Q is selected from the group consisting of:

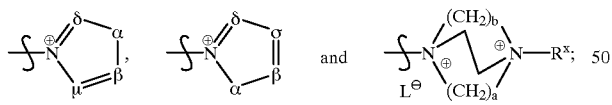

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2 R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O) NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

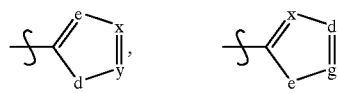

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

21. A compound according to claim 1 represented by formula Ib:

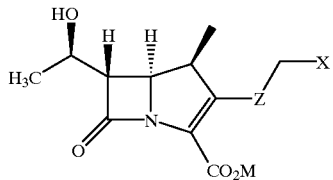

wherein X is:

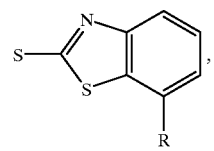

2

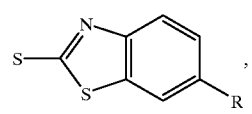

3

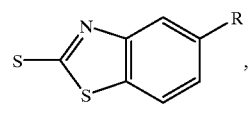

4

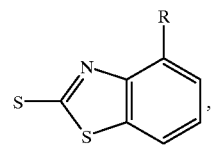

5 wherein:

R represents

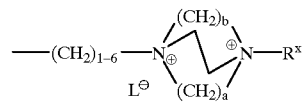

and $R^x$, a, b and $L^-$ are as originally defined.

22. A compound according to claim 20 wherein R represents A—$(CH_2)_n$—Q, wherein A is O, S, or $CH_2$, n is 0–3 and Q is selected from the group consisting of:

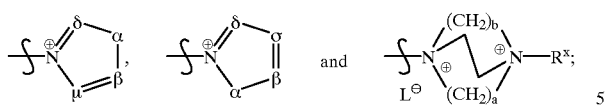

wherein L⁻, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2 R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O) NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups.

23. A compound which is

E-1

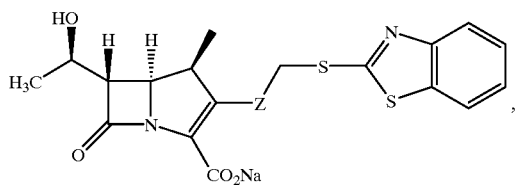

E-2

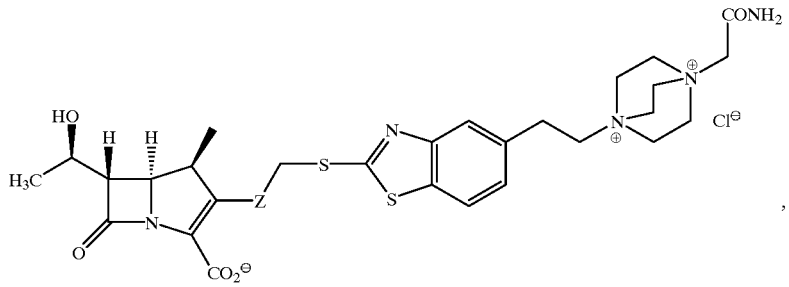

E-3

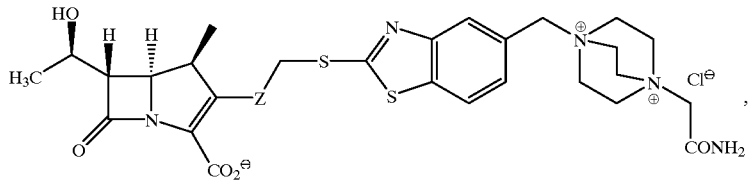

E-4

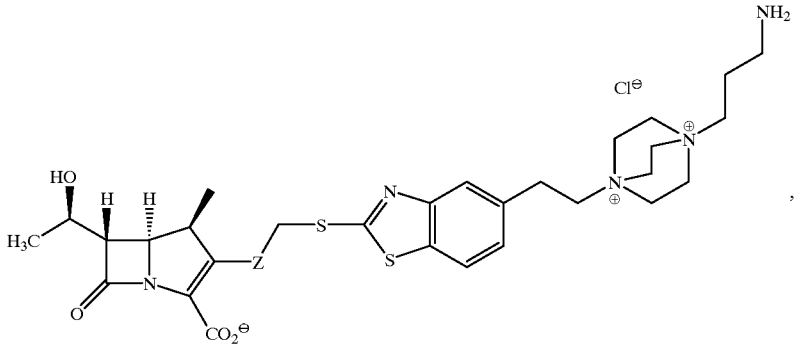

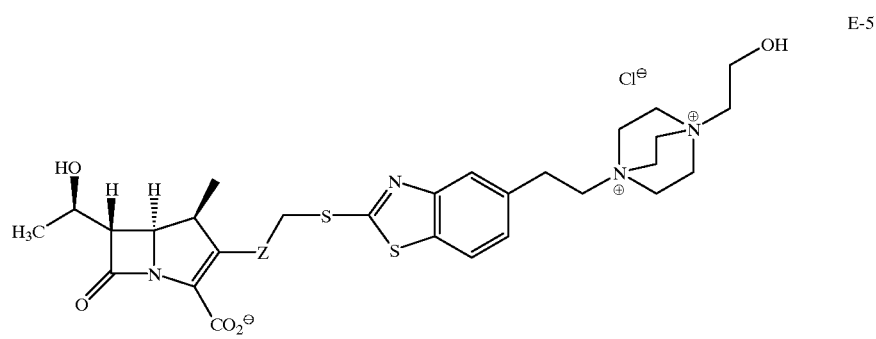
E-5
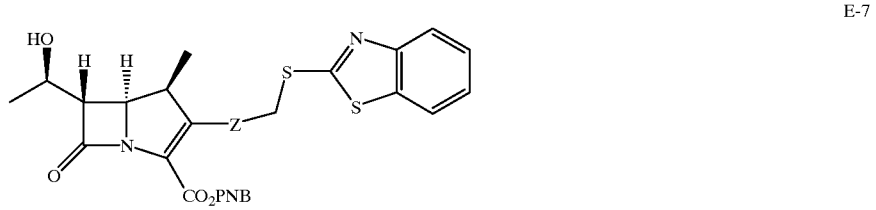
E-7
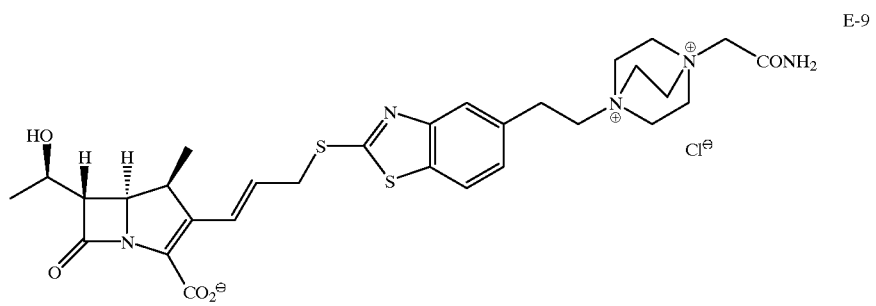
E-9
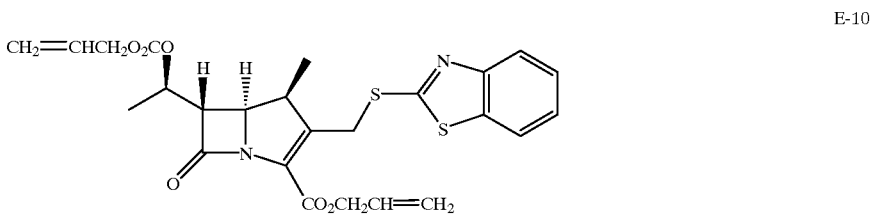
E-10
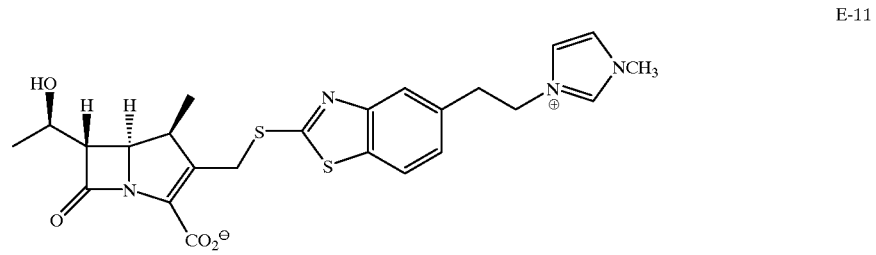
E-11
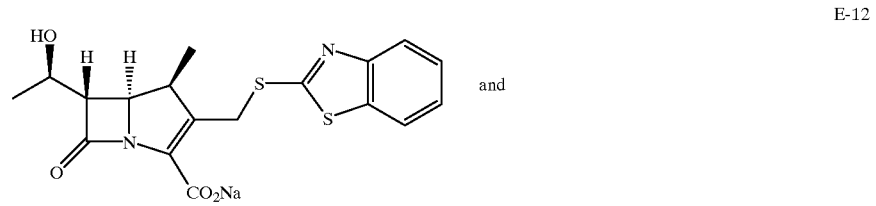
E-12

-continued

E-14

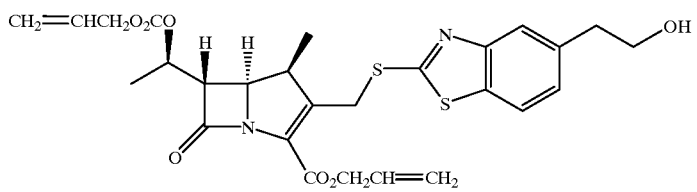

or a pharmaceutically acceptable acceptable salt thereof, wherein Z represents trans-ethenediyl, ethynediyl or is absent, PNB is p-nitrobenzyl.

24. A pharmaceutical composition comprised of a compound in accordance with claim 1 in combination with a pharmaceutically acceptable carrier.

25. A method of treating or preventing a bacterial infection in a mammalian patient in need thereof, comprising administering to said patient an effective amount of a compound of claim 1.

* * * * *